United States Patent [19]

Hirao et al.

[11] Patent Number: 4,876,088

[45] Date of Patent: Oct. 24, 1989

[54] GAMMA-GLOBULIN INJECTABLE SOLUTIONS CONTAINING SORBITOL

[75] Inventors: Yutaka Hirao; Kazuo Takechi, both of Osaka; Katuhiro Uriyu, Nara; Yahiro Uemura, Osaka, all of Japan

[73] Assignee: Green Cross Corporation, Osaka, Japan

[21] Appl. No.: 152,217

[22] Filed: Feb. 5, 1988

[30] Foreign Application Priority Data

Feb. 6, 1987 [JP] Japan ................................. 62-27031

[51] Int. Cl.$^4$ ..................... A61K 39/395; C08L 89/00
[52] U.S. Cl. .................................. 424/85.8; 424/101; 514/8; 514/21; 514/777; 530/387
[58] Field of Search ................ 424/101, 858; 530/387; 514/21, 8, 777

[56] References Cited

U.S. PATENT DOCUMENTS 4,396,608  8/1983  Tenold ............................ 424/101 X
4,412,990  11/1983  Lundblad et al. ............... 424/101 X
4,439,421  3/1984  Hooper et al. ......................... 424/85
4,440,679  4/1984  Fernandes et al. ............. 530/381 X
4,477,432  10/1984  Hardie ................................... 424/85

OTHER PUBLICATIONS

The Lancet, Nov. 19, 1983, Welch et al., pp. 1198–1199.

*Primary Examiner*—Howard E. Schain
*Attorney, Agent, or Firm*—Sughrue, Mion, Zinn, Macpeak & Seas

[57] ABSTRACT

An intravenously injectable solution of chemically unmodified γ-globulin having a complete molecular structure is disclosed, said solution containing sorbitol as a stabilizer and having a low electrical conductivity and a pH of about 5.5±0.2. The injectable solution does not cause an increase of γ-globulin polymer, a rise of anti-complement titer, or impairment of the activities of the γ-globulin, either during preservation or upon administration to a living body.

5 Claims, No Drawings

GAMMA-GLOBULIN INJECTABLE SOLUTIONS CONTAINING SORBITOL

FIELD OF THE INVENTION

This invention relates to a solution of chemically unmodified complete molecular type γ-globulin which can be administered intravenously.

BACKGROUND OF THE INVENTION

Preparations of chemically unmodified immunoglobulin which constitute plasma protein, and particularly preparations containing IgG as a main ingredient have been widely used for treatment and prophylaxis of various infectious diseases. Since γ-globulin is readily polymerized in a dissolved state which causes side effects when administered intravenously, it has hitherto been formulated into freeze-dried preparations. The freeze-drying method is also believed to be the best form for storing the γ-globulin from the standpoint of lability of chemically unmodified γ-globulin having a complete molecular structure when dissolved. Accordingly, the importance of freeze-drying is generally recognized.

On the other hand, liquid preparations are advantageous over the freeze-dried preparations due to convenience of administration because liquid preparations are free of the need to be dissolved, for example, in injectable distilled water on use. However, the above-mentioned lability of γ-globuloin has retarded the practical application of liquid preparations of γ-globlulin.

A γ-globulin liquid composition having a pH of from about 3.5 to 5 and an ionic strength of less than about 0.001 has recently been proposed as a stable liquid preparation as disclosed in U.S. Pat. No. 4,396,608 or European Patent Publication No. 73371A. However, such a strongly acidic liquid preparation is not always favorable when administered to a living body because the γ-globulin is liable to aggregate (i.e., to polymerize) in body fluids maintained substantially neutral due to the buffering capacity of such body fluids.

SUMMARY OF THE INVENTION

One object of this invention is to provide an intravenously injectable solution of chemically unmodified complete molecular type γ-globulin which does not cause an increase of γ-globulin polymer, a rise of anticomplement titer, or impairment of the activities of the γ-globulin, either during preservation or upon administration to a living body.

The above object of this invention can be accomplished by an intravenously injectable solution which comprises a low-conductive solution containing chemically unmodified complete molecular type γ-globulin, said solution further containing sorbitol and having a pH of about 5.5±0.2.

DETAILED DESCRIPTION OF THE INVENTION

The terminology "chemically unmodified complete molecular type γ-globulin" as used herein means γ-globulin possessing the following properties:

(a) It remains intact without undergoing any modification or change. Therefore, it does not contain γ-globulin fragments, such as Fab, F(ab')₂, Fc, etc.

(b) It shows neither reduction of antibody titer nor antibody spectrum as compared with intact γ-globulin.

(c) Its anticomplementary activity (complement fixation activity) is sufficiently lower than 20 units ($CH_{50}$) which is regarded safe based on Japan Biological Preparation Standard according to Notification No. 159 (October 1985) issued by Ministry of Public Welfare of Japan. (One unit in terms of $CH_{50}$ is defined as the amount of complement necessary to hemolyze half the amount of $5 \times 10^8$ cells of sensitized erythrocyte in 7.5 ml of a reaction mixture having a certain ionic strength and pH value, and a certain amount of $Ca^{++}$ and $Mg^{++}$ under the reaction of 60 minutes at 37° C.)

(d) It contains more than 95% by weight of the γ-globulin monomer based on the total weight of the γ-globulin.

The process for obtaining the chemically unmodified complete molecular type γ-globulin which can be used in the present invention is not restricted as long as intact γ-globulin having a low anticomplement titer can be obtained. The most efficient process comprises treating γ-globulin for intramuscular injection, which can be prepared using pre-existing facilities and has already been employed as a biological, with an acid and separating the resulting agglomerate. Putting aside the question as to complexity of processes involved and reduction in yield, it would be preferable to use γ-globulin having a low anticomplement titer which is obtained by treating γ-globulin with a nonionic surface active agent to remove γ-globulin agglomerates causative of complement fixation.

Typical processes for preparing the chemically unmodified complete molecular type γ-globulin will be described below.

Starting Material:

A fraction containing immunoglubulin is used as a starting material. This fraction is not particularly limited in so far as it originates from human serum and contains an immunoglobulin fraction. Specific examples of such an immunoglobulin-containing fraction include Fraction II+III and Fraction II obtainable by ethanol fractionation of Cohn (E. J. Cohn et al., J. Am. Chem. Soc., 68, 459 (1946)), and pastes of immunoglobulin-containing fractions equivalent thereto. The starting material may contain impurities, such as human blood-group antibodies, kallikrein, prekallikrein, IgM, IgG polymers, etc. (1) Polyethylene Glycol (PEG) Treatment:

The starting γ-globulin-containing fraction is terated with a low concentration of PEG, and the supernatant liquor is recovered.

The starting material is first suspended in an appropriate aqueous solvent. The aqueous solvent may contain sodium chloride, sodium phosphate, potassium phosphate, acetic acid, sodium acetate, citric acid, sodium citrate, etc.

The resulting suspention is treated with PEG having a molecular weight of from about 1,000 to 10,000, and preferably from about 2,000 to 6,000. The treatment can be carried out, for example, by mixing the suspension and PEG while stirring, usually at a temperature of from 0 to 4° C. for a period of from 30 minutes to 6 hours. Recommended treatment conditions are: a protein concentration of from 1 to 20 w/v %, and preferably from 5 to 15 w/v %; a PEG concentration of from 4 to 10 w/v %, and preferably from 4 to 8 w/v %; a pH of from 4 to 6 and preferably from 4.5 to 5.5; and an ionic strength of from 0.0001 to 0.1 M, and preferably from 0.0001 to 0.01 M.

The mixture is then subjected, for example, to centrifugation at 6,000 to 8,000 rpm for 10 to 30 minutes to recover the supernatant liquor.

The supernatant liquor thus separated is then treated with a high concentration PEG, and a precipitate is recovered as follows.

he supernatant liquor is treated with PEG having a molecular weight of from 1,000 to 10,000, and preferably from 2,000 to 6,000. The treatment can be carried out, for example, by mixing the supernatant liquor and PEG at 0° to 4° C. for 30 minutes to 6 hours. Recommended conditions for the treatment are: a protein concentration of from 1 to 20 w/v %, and preferably from 5 to 15 w/v %; a PEG concentration of from 10 to 15 w/v %, and preferably from about 11 to 13 w/v %; a pH of from 6 to 9, and preferably from 7.5 to 8.5; and an ionic strength of from 0.0001 to 0.1 M, and preferably from 0.0001 to 0.01 M.

The mixture is then subjected, for example, to centrifugation at 6,000 to 8,000 rpm for 10 to 30 minutes to recover the precipitate. (2) Anion Exchange Treatment:

This process comprises dissolving a γ-globulin-containing fraction in an aqueous solvent and contacting the solution with an anion exchanger to recover the non-adsorbed fraction. The treatment with an anion exchanger is particularly effective to remove IgM or IgG polymers.

The anion exchenger to be used comprises anion exchanging groups bonded to an insoluble carrier. The anion exchanging groups include diethylaminoehtyl (DEAE), a quaternary aminoehtyl (QAE) groups, etc., and the insoluble carrier includes agarose, cellulose, dextran, polyacrylamide, etc.

A γ-globulin-containing precipitate is dissolved in an appropriate aqueous solvent having a pH of from 5 to 8 and a low ionic strength, and preferably an ionic strength of from 0.0001 to 0.1 M. The aqueous solvent may contain the solutes as described in Process 1) above. The protein concentration of the resulting solution preferably ranges from 1 to 15 w/v %, and more preferably from 3 to 10 w/v %.

The γ-globulin solution is then contacted with an anion exchanger equilibrated with the same aqueous solvent as used above, either in a batch system or in a continuous system. For instance, batchwise treatment can be carried out by mixing the γ-globulin solution with an anion exchanger in an amount of from about 10 to 100 ml per ml of the anion exchanger, stirring the mixture at 0° to 4° C. for about 0.5 to 2 hours, and centrifuging the mixture at 6,000 to 8,000 rpm for 10 to 30 minutes to recover the supernatant liquor. Continuous treatment can be effected by passing the γ-globulin solution through a column of an anion exchanger at a rate of from about 10 to 100 ml per ml of the anion exchanger and recovering the non-adsorbed fraction.

(3) Treatment with Fixed Diamino Compound:

This process comprises contacting a γ-globulin-containing fraction with a fixed diamino compound and recovering a non-adsorbed fraction. The treatment with a fixed diamino compound is particularly effective to remove prekallikrein or kallikrein.

The fixed diamino compound to be used is a diamino compound fixed to an insoluble carrier. The diamino compound includes aminobenzamidine, aminobenzguanidine, lysine, arginine, etc., and the insoluble carrier includes agarose, cellulose, dextran, silica gel, glass, etc.

Fixation of the diamino compound to the insoluble carrier can be effected by any known technique. For example, the diamino compound can be fixed to agarose, cellulose, or the like carrier by a CNBr activation method (Axen, R. et al., Nature, 214, 1302 (1967)); or to silica gel, glass or the like carrier by an oxirane method (Cuatreasas, P. et al., Biochemistry, 11, 2291 (1972)).

A γ-globulin-containing fraction is contacted with the fixed diamino compound under conditions of from 1 to 5 w/v %, and preferably from 3 to 10 w/v %, in protein concentration; from 5 to 8, and preferably from 6 to 7, in pH; and from 0.0001 to 0.1 M, and preferably from 0.0001 to 0.01 M, in ionic strength, either in a batch system or in a continuous system.

For example, in a batch system, from about 10 to 100 ml of the fraction is mixed with 1 ml of the fixed diamino compound, and the mixture is stirred at 0° to 10° C., and preferably 0° to 4° C., for 0.5 to 4 hours, and preferably about 40 minutes to 2 hours, followed by centrifugation at 6,000 to 8,000 rpm for 10 to 30 minutes to recover the supernatant liquor.

In a continuous system, the fraction is passed through a column of the fixed diamino compound in an amount of from anout 10 to 100 ml per ml of the fixed diamino compound, and the non-adsorbed fraction is recovered.

(4)Treatment with Fixed Human Blood-Group Substance:

This process comprises contacting a γ-globulin-containing fraction with a fixed human blood-group substance to recover a non-adsorbved fraction, and is particularly suited for removal of human blood-group antibodies.

The fixed human blood-group substance to be used is a human blood-group substance fixed to an insoluble carrier. The human blood-group substance can be prepared by any known technique. For example, erythrocytes of human blood-groups A, B, AB, or O are subjected to hemolysis in a hypotonic solution or ultrasonic treatment and then purified by ammonium sulfate fractionation or PEG fractionation.

The thus prepared human blood-group substance is dissolved in physiological saline and heat-treated at temperatures effective for inactivation of viruses present, e.g., between about 50° and 70° C., and preferably about 60° C., for 7 to 13 hours, and preferably about 10 hours, or between about 80° and 130° C., and preferably between about 95° and about 121° C., for about 1 to 40 minutes, and preferably 2 to 30 minutes. Thereafter, the solution is centrifuged to remove any insoluble matter. The supernatant liquor is then subjected to dialysis against distilled water to obtain a human blood-group A, B, AB, or O substance, respectively.

The insoluble carrier to which the human blood-group susbtance is fixed includes agarose, cellulose, dixtran, silica gel, glass, etc.

Fixation can be carried out in a known manner. For example, the human blood-group substance can be fixed to agarose, cellulose or the like carrier by a CNBr activation method or to silica gel, glass or the like carrier by an oxirane method.

A γ-globulin-containing fraction is contacted with the fixed human blood-group substance having been equilibrated with the above-described aqueous solvent under conditions of a protein concentration ranging from 1 to 15 w/v %, and preferably from 3 to 10 w/v %, a pH of from 5 to 8, and preferably of from 6 to 7, and an ionic concentration ranging from 0.0001 to 0.1

M, and preferably from 0.0001 to 0.01 M, either in a batch system or in a continuous system.

For example, in a batch system, the γ-globulin-containing fraction is mixed with the fixed human blood-group substance in an amount of from about 10 to 100 ml per ml of the fixed human blood-group substance, and the mixture is stirred at 0° to 10° C., and preferably 0° to 4° C., for 30 minutes to 4 hours, and preferably about 30 minutes to 2 hours, followed by centrifugation at 6,000 to 8,000 rpm for 10 to 30 minutes to recover the supernatant liquor.

In a continuous system, about 10 to 100 ml of the fraction is passed through a column of 1 ml of the fixed human blood-group substance, and the non-adsorbed fraction is recovered.

(5) Heat Treatment:

According to this process, a γ-globulin-containing fraction is heated in the presence of a stabilizer under such conditions that impurities, e.g., HB virus, AIDS virus, etc., are compretely inactivated while minimizing reduction of antibody activities of immunoglobulin. The heat treatment is carried out in a dry state having a water content of 3% or less (i.e., dry heat treatment) or in a dissolved state in the form of an aqueous solution (i.e., wet heat treatment).

The stabilizer which can be used in either the dry or wet heat treatment preferably includes disaccharides (e.g., sucrose, maltose, etc.) and suger alcohols (e.g., sorbitol, mannitol, etc.).

A recommended amount of the stabilizer to be added is from 0.5 to 5 w/v %, and preferably from 1 to 3 w/v %, in the dry heat treatment, or 10 w/v % or more, and preferably from 10 to 50 w/v %, in the wet heat treatment.

It is desireble that the protein concentraiton of the γ-globulin-containing fraction to be heat-treated be adjusted to between 1 and 10 w/v %, and preferably to between 3 and 7 w/v %, for the dry heat treatment, or to between 0.1 to 30 w/v %, and preferably to between 5 and 20 w/v %, for the wet heat treatment.

In the case of the dry heat treatment, after a stabilizer is added to the γ-globulin fraction, if desired, followed by sterilization by filtration, the water content of the fraction is adjusted to 3% or less, and preferably 1% or less by, for example, freeze-drying. Freeze-drying can be carried out, for example, at a temperature of from 20° to 40° C. for a period of from about 24 to 96 hours in vacuo of 0.5 mmHg. Then, the fraction is heated at a temperature of from 50° to 70° C., and preferably at about 60° C., for a period of from 10 to 200 hours, and preferably of from about 50 to 100 hours. Stability of the immunoglobulin during the heating can be ensured by conducting the heat treatment in an inert gas atmosphere, such as nitrogen, argon, helium, etc.

In the case of the wet heat treatment, after the aqueous solution of the Y-globulin-containing fraction is adjusted to a pH of from 4.5 to 6.5, and preferably from 5 to 6, the solution is heated at 50° to 70° C., and preferably about 60° C., for 10 minutes to 20 hours, and preferably about 10 hours.

Preparation and purification of the γ-globulin to be used in the present invention can be achieved by appropriately combining the above-descirbed processes according to the purpose. In a prefered embodiment the starting material is subjected to wet hear treatment, PEG teratment, blood-group substance treatment, and anion exchange treatment in this order.

The thus prepared chemically unmodified complete molecular type γ-globulin is dissolved in water in a usual manner to prepare and aqueous solution in concentrations ranging from 1 to 10 w/v %, and preferably from 3 to 7 w/v %. Sorbitol is then added thereto in concentrations of from 1 to 10 w/v %, and preferably from 2 to 10 w/v %, and the solution is adjusted so as to have a pH of $5.5 \pm 0.2$, and preferably about 5.5, and a low electrical conductivity, and preferably not more tha 1 mmho, and more preferably not more than 0.6 mmho. The resulting solution is further subjected to working-up procedures commonly employed in the art, such as sterilization by filtration, pouring into vials, and the like, to obtain intravenously injectable liquid preparations of chemically unmodified complete molecular type γ-globulin.

Throughout the above-described processes, a pH value of a reaction mixture is adjusted using 0.5 N NaOH or 0.5 N HCl, and electrical conductivity is measured at 8° C. with a conductivity measuring apparatus.

Dose of the γ-globulin of the present invention for intravenous injection is the same as a conventional intravenously injectable γ-globulin, i.e., about 500 to 5,000 mg.

The chemically unmodified complete molecular type γ-globulin liquid preparations according to the preset invention undergo neither an increase of γ-globulin polymers nor a rise of anticomplement titer either during long-term preservation or upon administration to a living body, and satisfactorily retain their appearance and properties when preserved for a long time.

The present invention is now illustrated in greater detail by way of Test Examples and an Example. In the test examples, testing methods were as follows.

(1) Appearance:

Turbidity of the liquid preparation that is of interest in connection with appearnce, was visually observed and rated as follows:

A: No abnormality (clear and cololess)
B: Slightly colored or turbid
C: Seriously colored or turbid Further, an absorbance at 600 nm was measured to evaluate appearance.

(2) Determination of Polymer Content:

The content of γ-globulin polymers based on the total weight of γ-globulin in the liquid preparation was determined by means of high performance liquid chromatography.

(3) Anticomplement Titer:

Merasured in accordance with Capat and Mayer, *Experimental Immunochemistry*, 225 (1961) and Nishioka & Okada, Men-eki no Seikaoaku (*Biochemistry in Immunology*), Vol. 103, Kyoritsu Shuppan (1971). That is, a sample was added to 100 units of complement, and the decrease in units of the complement was measured and taken as the anticomplement titer.

(4) Measles Antibody Titer:

Measured in accordance with the hemagglutination inhibition test method (Rosen, L., Virology, 13, 139 (1961)), and expressed by an international unit (IU/100 mg).

Each chemically unmodified complete molecular type γ-globulin-containing composition prepared in the following test examples was heat-treated at 56° C. for 60 minutes and the stability of the composition was evaluated. In Test examples and Example, distilled water was used as a solvent. A pH value of the preparation was adjusted using 0.5 N NaOH or 0.5 N HCl and electrical conductivity was measured with a conductivity measuring apparatus, CD-35MII model (M & S Instrument Co.).

TEST EXAMPLE 1

A liquid composition of chemically unmodified complete molecular type γ-globulin having a γ-glubulin concentration of 5 w/v %, an electrical conductivity of 1 mmho (measured at 8? C.), and a pH of 5.5 was prepared. Each of stabilizers shown in Table 1 below was added to a concentration of 5 w/v %, and the resulting liquid preparation was tested. The results obtained are shown in Table 1.

TABLE 1

| Stabilizer | Appearance | Absorbance at 600 nm | Polymer Content (wt %) |
|---|---|---|---|
| Glucose | C | — | — |
| Galactose | C | — | — |
| Sucrose | A | 0.013 | 28.62 |
| Lactose | C | — | — |
| Maltose | C | — | — |
| Sorbitol | A | 0.015 | 4.58 |
| Mannitol | B | 0.024 | — |
| Albumin | C | — | — |
| None (heated) | C | — | — |
| None (non-heated) | A | 0.004 | 0.00 |

It can be seen from Table 1 that addition of sorbitol achieved satisfactory results.

TEST EXAMPLE 2

A liquid composition of chemically unmodified complete molecular type γ-globulin having γ-globulin concentration of 5 w/v %, an electrical conductivity of 1 mmho (measured at 8° C.), and a varied pH value as shown in Table 2 below and containing 5 w/v % of sorbitol or sucrose as stabilizer was prepared. The test results are shown in Table 2.

TABLE 2

| | Sorbitol | | Sucrose | |
|---|---|---|---|---|
| pH | Appearance | Polymer Content (wt %) | Appearance | Polymer Content (wt %) |
| 3.5 | A | >10 | A | >10 |
| 4.0 | A | >10 | A | >10 |
| 4.5 | A | >10 | A | >10 |
| 5.0 | A | 5.38 | — | >10 |
| 5.5 | A | 4.24 | A | >10 |
| 5.5 (non-heated) | A | 0.00 | A | 0.00 |
| 6.0 | A | 5.28 | A | >10 |
| 7.0 | B | — | B | — |
| 8.0 | C | — | C | — |
| 9.0 | B | — | B | — |
| 10.0 | A | >10 | A | >10 |

As is apparent from Table 2, γ-globulin is particularly stable at a pH of around 5.5 in the presence of sorbitol.

TEST EXAMPLE 3

A liquid composition of chemically unmodified complete molecular type γ-globulin having a γ-globulin concentration of 5 w/v %, a sorbitorl concentration of 5 w/v %, a pH of 5.5, and a varied electrical conductivity (measured at 8° C.) as shown in Table 3 below was prepared. Test results are shown in Table 3.

TABLE 3

| Electrical Conductivity (mmho) | Appearance | Polymer Content (wt %) |
|---|---|---|
| 0.5 (non-heated) | A | 0.00 |
| 0.5 | A | 4.20 |
| 1 | A | 7.10 |
| 2 | C | — |
| 5 | C | — |
| 10 | C | — |

It can be seen that γ-globulin shows particular stability when the preparation had an electrical conductivity of 1 mmho or less.

TEST EXAMPLE 4

A liquid preparation of chemically unmodified complete molecular type γ-globulin having a γ-globulin concentration of 5 w/v %, an electrical conductivity of 0.5. mmho (measured at 8° C.), a pH of 5.5, and a varied sorbitol concentration as shown in Table 4 was prepared. The test results obtained are shown in Table 4.

TABLE 4

| Sorbitol Concentration (w/v %) | Appearance | Polymer Content (wt %) |
|---|---|---|
| 0 | C | — |
| 1 | C | — |
| 2 | A | 12.24 |
| 5 | A | 4.06 |
| 8 | A | 3.29 |
| 10 | A | 2.34 |
| 15 | A | 0.10 |
| 20 | A | 0.03 |

As can be seen from Table 4, stability of γ-globulin increases with the sorbitol concentration.

TEST EXAMPLE 5

A chemically unmodified complete molecular type γ-globulin liquid composition having a γ-globulin concentration of 5 w/v %, a sorbitol concentration of 5 w/v % (for rendering the composition physiologically isotonic), a pH of 5.5 and an electrical conductivity of 0.5 mmho (measured at 8° C.) was prepared. The composition was found to be clear and colorless and to have a polymer content of 0.00 wt %, an anticomplement titer ($CH_{50}$/ml) of 8, and a measles antibody titer (IU) of 32.

The preservation stability of the composition was evaluated in terms of appearance, polymer content, anticomplement titer, and a measles antibody titer, and the results obtained are shown in Table 5.

TABLE 5

| Temperature (°C.) | Appearance | | | Polymer Content (wt %) | | | Anticomplement Titer ($CH_{50}$/ml) | | | Measles Antibody Titer (IU) | | |
|---|---|---|---|---|---|---|---|---|---|---|---|---|
| | 1 Mth. | 3 Mths. | 6 Mths. | 1 Mth. | 3 Mths. | 6 Mths. | 1 Mth. | 3 Mths. | 6 Mths. | 1 Mth. | 3 Mths. | 6 Mths. |
| 11 | colorless | colorless | colorless | 0.00 | 0.02 | 0.01 | 7 | 9 | 9 | 32 | 32 | 32 |

TABLE 5-continued

| Temperature (°C.) | Appearance | | | Polymer Content (wt %) | | | Anticomplement Titer (CH$_{50}$/ml) | | | Measles Antibody Titer (IU) | | |
|---|---|---|---|---|---|---|---|---|---|---|---|---|
| | 1 Mth. | 3 Mths. | 6 Mths. | 1 Mth. | 3 Mths. | 6 Mths. | 1 Mth. | 3 Mths. | 6 Mths. | 1 Mth. | 3 Mths. | 6 Mths. |
| 25 | clear colorless | clear colorless | clear colorless | 0.00 | 0.02 | 0.03 | 8 | 8 | 10 | 32 | 32 | 32 |
| 37 | clear colorless clear | clear colorless clear | clear colorless clear | 0.02 | 0.08 | 0.14 | 12 | 16 | 22 | 32 | 32 | 32 |

EXAMPLE 1

In 10 liters of distilled water was suspended 1 Kg of a Cohn fraction II+III paste. After adjusting to a pH of 5.5, the suspension was subjected to centrifugation. The supernatant liquor was recovered, and 50 g of sorbitol was added thereto per 100 ml so as to have a final concentration of 33 w/v %, followd by heating at 60° C. for 10 hours. After the heat treatment, the mixture was adjusted to a pH of 5.5, and PEG #4000 was added thereto so as to have a final concentration of 6 w/v %, followed by centrifugation at 2° C.

The recovered supernatant liquor was adjusted to a pH of 8.0 with a 1N sodium hydroxide aqueous solution. PEG #4000 was again added thereto to a final concentration of 12 w/v %, followed by centrifugation to obtain an IgG fraction as a precipitate.

The resulting fraction was dissolved in water, and 100 ml of the IgG solution was passed through a column packed with 3 ml of human blood-group substance fixed to Formyl Cellulofine ® (Seikagaku Kogyo Co., Ltd.) having been equilibrated with distilled water to thereby adsorb human blood antibodies thereto. By this adsorption treatment, the blood-group antibody titer decreased from (1:32) to (1:2).

To the resulting solution was added 1 ml of DEAE-Sephadex ® per 50 ml of the solution, and the mixture was stirred at 0° to 4° C. for about 1 hour, followed by centrifugation at 7,000 rpm for about 20 minutes to recover an IgG solution as a supernatant.

The resulting IgG solution was diluted with distilled water so as to have an IgG concentration of 5 w/v %. After adjusting to a pH of about 5.5 with a sodium acetate aqueous solution, sorbitol was added thereto to a final concentration of 5 w/v %. The resulting aqueous solution was found to have an electrical conductivity of about 1 mmho. The solution was sterilized by filteration to obtain an intravenously injectable solution of immunoglobulin.

While the present invention has been described in detail and with reference to specific embodiments thereof, it will be apparent to one skilled in the art that various changes and modifications can be made therein without departing from the spirit and scope thereof.

What is claimed is:

1. An intravenously injectable solution of chemically unmodified gamma-globulin having a complete molecular structure, said solution containing sorbitol in a concentration of from 1 to 20% by weight per volume as a stabilizer and having a low electrical conductivity and a pH of about 5.5±0.2, said solution having an electrical conductivity of not higher than 1 mmho as measured at 8° C.

2. An intravenously injectable solution as claimed in claim 1, wherein more than 95% by weight of said γ-globulin is γ-globulin monomer.

3. An intravenously injectable solution as claimed in claim 1, wherein said solution has an electrical conductivity of not higher than 0.6 mmho as measured at 8° C.

4. An intravenously injectable solution as claimed in claim 1, wherein said sorbitol is present in a concentration of from 2 to 10% by weight per volume.

5. An intravenously injectable solution as claimed in claim 1, wherein said solution has a pH of about 5.5.

* * * * *

UNITED STATES PATENT AND TRADEMARK OFFICE
CERTIFICATE OF CORRECTION

PATENT NO. :   4,876,088

DATED      :   October 24, 1989

INVENTOR(S) :  Hirao, et al.

It is certified that error appears in the above-identified patent and that said Letters Patent is hereby corrected as shown below:

TITLE PAGE, Item [21]

Please correct the application no. to read -- 152,717 --.

Signed and Sealed this

Sixteenth Day of July, 1991

Attest:

HARRY F. MANBECK, JR.

*Attesting Officer*                *Commissioner of Patents and Trademarks*